(12) United States Patent
Giraud

(10) Patent No.: US 9,248,950 B2
(45) Date of Patent: Feb. 2, 2016

(54) PLUNGER FOR MOISTURE TIGHT DISPENSER

(71) Applicant: Jean-Pierre Giraud, Auburn, AL (US)

(72) Inventor: Jean-Pierre Giraud, Auburn, AL (US)

(73) Assignee: CSP Technologies, Inc., Auburn, AL (US)

( * ) Notice: Subject to any disclaimer, the term of this patent is extended or adjusted under 35 U.S.C. 154(b) by 0 days.

(21) Appl. No.: 14/308,228

(22) Filed: Jun. 18, 2014

(65) Prior Publication Data

US 2014/0299623 A1 Oct. 9, 2014

Related U.S. Application Data

(63) Continuation-in-part of application No. PCT/US2013/020068, filed on Jan. 3, 2013.

(60) Provisional application No. 61/582,656, filed on Jan. 3, 2012.

(51) Int. Cl.
*B65D 83/00* (2006.01)
*B65D 83/08* (2006.01)
*B65D 21/08* (2006.01)
*G01N 33/487* (2006.01)

(52) U.S. Cl.
CPC .......... *B65D 83/0864* (2013.01); *B65D 21/086* (2013.01); *G01N 33/48757* (2013.01)

(58) Field of Classification Search
CPC .................. B65D 83/0858; B65D 83/0864
USPC ............ 221/279, 65, 186, 187, 190, 209, 246
See application file for complete search history.

(56) References Cited

U.S. PATENT DOCUMENTS

| | | | | |
|---|---|---|---|---|
| 3,861,563 | A * | 1/1975 | Lisbin et al. | 221/279 |
| 4,142,863 | A * | 3/1979 | Covington et al. | 422/63 |
| 5,197,631 | A * | 3/1993 | Mishima | 221/52 |
| 5,366,113 | A * | 11/1994 | Kim et al. | 221/232 |
| 6,136,352 | A * | 10/2000 | Silverstein et al. | 426/115 |
| 6,378,702 | B1 * | 4/2002 | Kintzig | 206/456 |
| 6,953,131 | B2 * | 10/2005 | Devine | 221/246 |
| 6,997,343 | B2 * | 2/2006 | May et al. | 221/232 |
| 7,273,156 | B2 * | 9/2007 | Gao et al. | 221/47 |
| 8,684,172 | B2 * | 4/2014 | Yao | 206/204 |
| 2004/0007585 | A1 * | 1/2004 | Griffith et al. | 221/232 |
| 2013/0292403 | A1 * | 11/2013 | Cote et al. | 221/92 |

* cited by examiner

*Primary Examiner* — Patrick Mackey
(74) *Attorney, Agent, or Firm* — David B. Gornish

(57) ABSTRACT

A dispenser includes a body, the body including a product housing defining an interior for housing a plurality of products. The product housing has a dispensing portion defining a dispensing opening configured to permit the removal of at least one of the plurality of products from the interior. The body further includes a plunger movably engaged with the product housing and including a product support that moves within the interior to move the plurality of products towards the dispensing opening, the dispenser comprising a moisture tight seal between the plunger and the product housing.

13 Claims, 4 Drawing Sheets

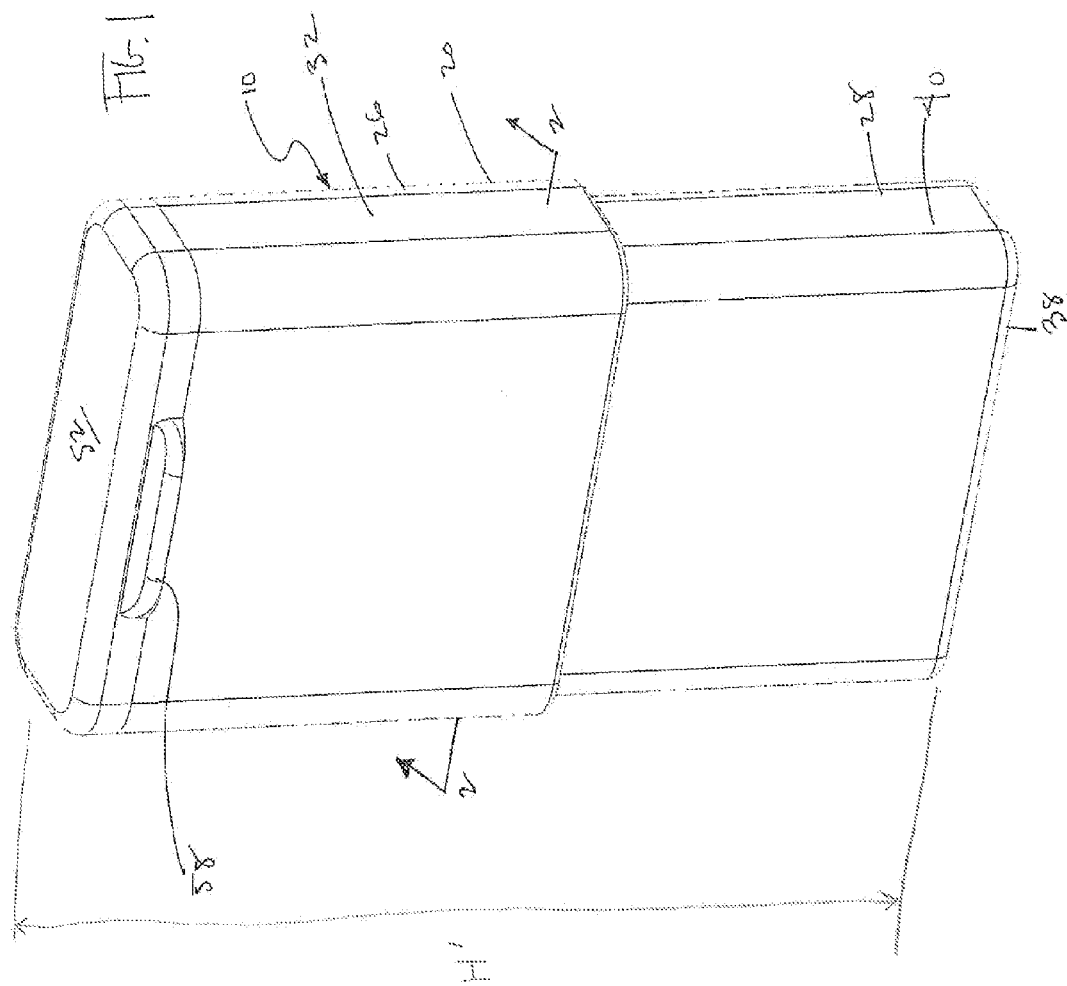

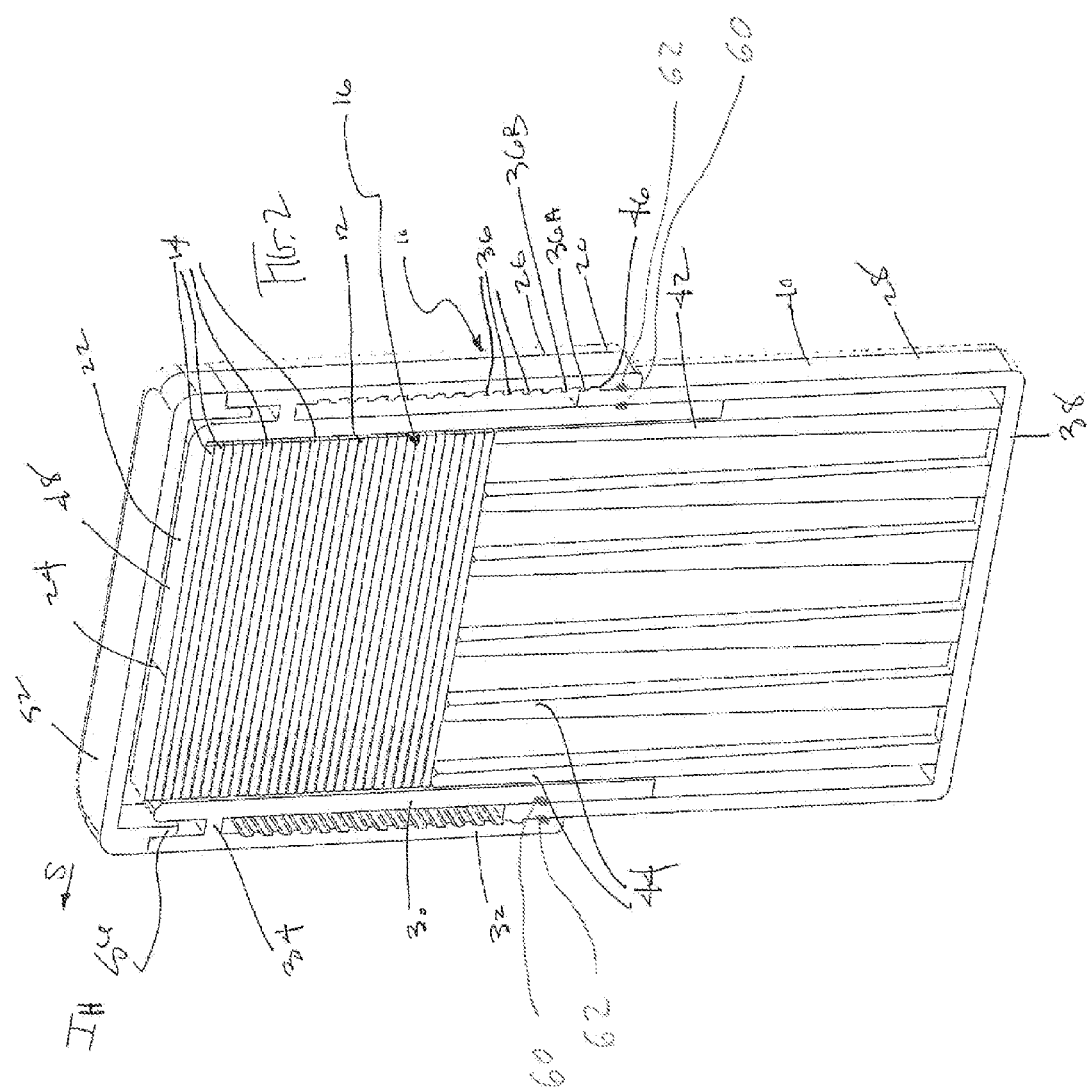

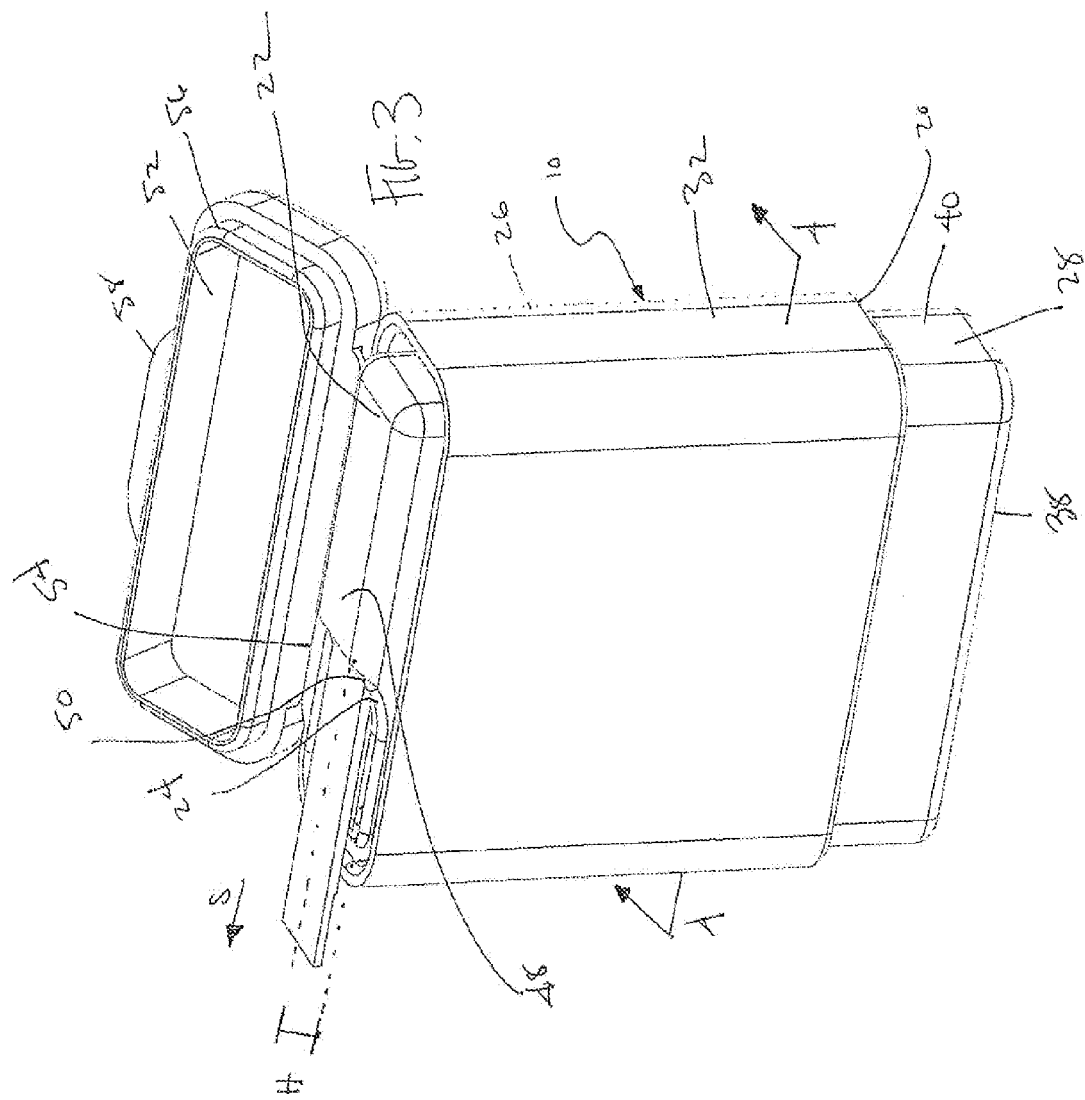

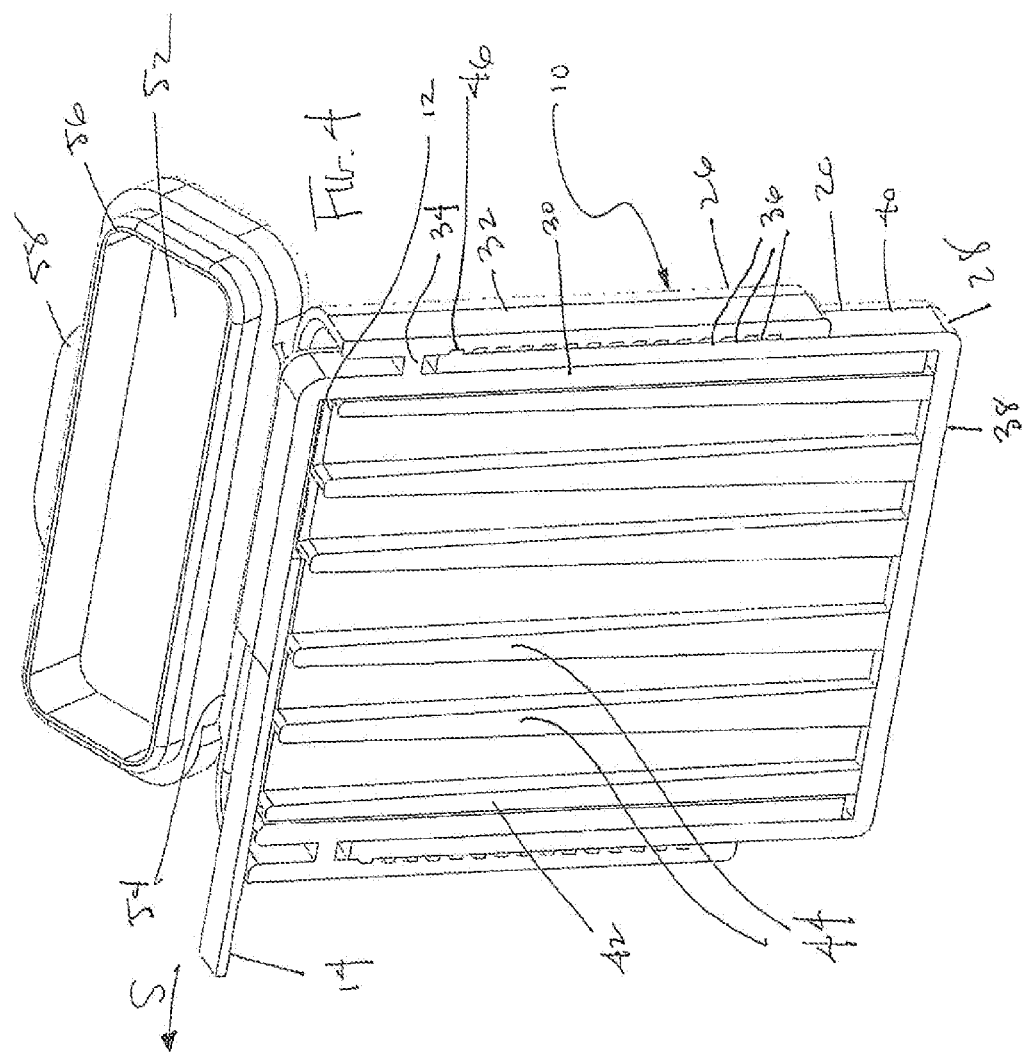

PLUNGER FOR MOISTURE TIGHT DISPENSER

CROSS-REFERENCE TO RELATED APPLICATIONS

This application is a continuation-in-part of International Patent Application PCT/US2013/020068, filed Jan. 3, 2013, which application claims the benefit of U.S. Provisional Patent Application No. 61/582,656, filed Jan. 3, 2012, all of which applications are incorporated herein by reference in their entireties.

SUMMARY

The present invention is directed to a dispenser including a dispensing portion defining a dispensing opening and a product housing defining an interior for housing a plurality of products. The dispenser further includes a plunger movably engaged with the product housing and having a product support that moves within the interior to force products towards the dispensing opening.

The present invention is further directed to a dispensing assembly including a plurality of products provided in a stack, a body that defines an interior for housing the stack, and a dispensing portion located at an end of the body and including a dispensing opening. The stack extends within the interior towards the dispensing portion, and a selected one of the products located at an end of the stack is aligned with the opening, so as to permit removal from the body during a dispensing operation.

BRIEF DESCRIPTION OF THE DRAWINGS

FIG. 1 is a perspective view of a loaded dispenser according to the invention, in a closed position;

FIG. 2 is a cross section taken along line 2-2 of FIG. 1;

FIG. 3 is a perspective view of a partially loaded dispenser according to the invention, in an opened position and during a dispensing operation; and FIG. 4 is a cross section taken along line 4-4 of FIG. 3.

DETAILED DESCRIPTION OF THE PREFERRED EMBODIMENTS

Certain terminology is used in the foregoing description for convenience and is not intended to be limiting. Words such as "front," "back," "top," and "bottom" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

A dispenser 10 according to the invention is shown in FIGS. 1-4. As shown, the dispenser defines an interior 12 that houses a plurality of products 14. In the illustrated embodiment, the products 14 are in the form of strips. Suitable products in strip form could be, for example, diagnostic test strips, such as blood glucose test strips. The dispenser 10 includes a body 20, which defines the interior 12 and houses the products 14, and a cap 52. The cap 52 moves between a closed position in which it closes off the body 20, as shown in FIGS. 1 and 2, and an opened position, in which it is displaced from the body 20 to expose a dispensing portion 22 thereof to allow a dispensing operation to take place, as shown in FIGS. 3 and 4. The products 14 within the interior 12 are provided in the form of a stack extending towards the dispensing portion 22 of the body. A selected product 14 located at an end of the stack 16 is aligned with an opening 24 of the dispensing portion to permit removal therefrom in a dispensing operation.

The body 20 of the dispenser 10 includes an upper product housing 26 and a lower plunger 28. The housing 26 includes an inner wall 30 and an outer wall 32, which is joined with the inner wall 30 by a connecting wall 34. As best shown in FIGS. 2 and 4, the inner wall 30 and outer wall 32 are both tubular and substantially parallel, with the inner wall 30 being located within the outer wall 32. The inner wall 30 and outer wall 32 are separated by a distance sufficient to allow receipt of the plunger side wall 40, as described in detail below. The tubular shape of the inner wall 30 and outer wall 32 may correspond to the shape of products 14, as best shown in FIG. 2, so as to allow the stack 16 of products to sit within inner wall 30 with little room for movement within. The connecting wall 34 extends between the inner wall 30 and outer wall 32 in a direction substantially perpendicular to both in the illustrated embodiment, but this is not a necessary feature of the invention. A plurality of ratchet teeth 36 are formed on an inner surface of the outer wall 32.

The plunger 28 includes a bottom wall 38, side wall 40, and product support 42. The bottom wall 38 forms the bottom of the dispenser 10 and the side wall 40 extends upwardly therefrom into a space formed between inner wall 30 and outer wall 32 of the housing 26. Product support 42 extends upwardly from the bottom wall 38 at a location within the side wall 40, as shown in FIGS. 2 and 4. When the side wall 40 is positioned between inner wall 30 and outer wall 32, product support 42 is located within the tubular perimeter of inner wall 30. A stack 16 of products 14 sits atop product support 42. In the illustrated embodiment, product support 42 is formed as a plurality of protrusions 44 extending upward from bottom wall 38. In other embodiments more or fewer protrusions 44 could be used, as well as a single protrusion, or a single component that completely fills the space within the housing 26 inner wall. Other components capable of supporting product stack 16 could be employed and would be recognizable to a person of ordinary skill in the art.

Side wall 40 includes a single ratchet tooth 46 on an outer surface thereof for engagement with the ratchet teeth 36 of outer wall 32. The engagement or ratchet tooth 46 with ratchet teeth 36 allows for only upward movement of the plunger 28 with respect to the housing 26, i.e., from the position shown in FIGS. 1 and 2, to the position shown in FIGS. 3 and 4, and does not permit downward movement of the plunger 28 with respect to the housing 26. Ratchet tooth 26 is provided at an upper portion of side wall 40 in the embodiment shown, in order to permit maximum upward movement of plunger 28 with respect to housing 26. In other embodiments, ratchet teeth 36 could be provided on an outer surface of inner wall 30 and ratchet tooth 46 could be provided on an inner surface of side wall 40. In yet other embodiments, ratchet teeth 36 could be provided on the inner or outer surface of side wall 40 and single ratchet tooth 46 provided on the inner surface of outer wall 32 or outer surface of inner wall 30. In yet another embodiment, ratchet teeth 36, 46 could be omitted entirely and side wall 40 slidably engaged between inner wall 30 and outer wall 32. A catch mechanism could optionally be provided in such an embodiment to prevent disengagement of the plunger from the housing 26.

The dispenser 10 is shown in a fully loaded state, having a complete stack 16 of products 14 housed therein, in FIGS. 1 and 2, and a partially loaded state, having only a single product 14 housed therein, in FIGS. 3 and 4. As shown, the plunger 28 of the dispenser 10 in the partially loaded state, as well as in an empty state (not shown), is located upward with respect to the plunger 28 of the dispenser 10 in the fully loaded state. The products 14 or stack of products 16 is located between the top of the product support 42 and the dispensing portion 22 of the body. In the fully loaded dispenser 10 of FIGS. 1 and 2 the height of the stack 16 is greater than the height of the single product 14 in the partially loaded dispenser of FIGS. 3 and 4, resulting in the upward placement of the plunger 28 in the partially loaded dispenser.

Each time a dispensing operation takes place as described below, a product 14 is removed from the stack 16, resulting in a reduction in height of the stack. A space between the top of the stack 16 and the dispensing portion 22 is thus formed. In order for a subsequent dispensing operation of another product 14 to take place, the plunger 28, and in turn the stack 16 must be moved upwards, in order to close the distance between the uppermost product 14 of the stack and the dispensing portion 22. As the plunger is moved up, ratchet tooth 46 of the plunger 28 side wall 40 becomes disengaged with the ratchet tooth 36A of housing 26 outer wall 32 with which it is currently engaged, and becomes engaged with a ratchet tooth 36B directly above it, locking the plunger 28 in its new upward position with respect to the housing 26 and holding uppermost strip 14 in its place in contact with dispensing portion 22 in anticipation for a subsequent dispensing operation.

In the illustrated embodiment, each ratchet tooth 36 permits upward movement of the plunger 28 at a distance approximately equal to the height of a single product, so as to always bring the uppermost product 14 in contact with dispensing portion 22 after a dispensing operation and upward movement of plunger 28.

The dispensing portion 22 is located at an upper area of housing 26. In the illustrated embodiment, the dispensing portion 22 includes a top wall 48 that partially closes off interior 12 and covers a portion of the uppermost product 14, and an opening 24. Top wall 48 restrains further upward movement of the stack 16 or some of the products 14 thereof during or after upward movement of plunger 28 as described above. It further retains products 14 within interior 12 until removed during a dispensing operation. Opening 24 is sized and shaped to permit removal of at least a single product 14 therefrom. In the illustrated embodiment, opening 24 is sized and shaped to permit removal of only a single product 14 at a time. In the illustrated embodiment, opening 24 extends between an end of top wall 48 and a portion of inner wall 30 at an angle. The angled edges 50 forming opening extend at a height H equal to or slightly more than that of a single product 14, and are aligned with an uppermost product 14, so as to allow uppermost product 14 to be slid in direction S, laterally out of the interior 12 through opening 24, for example by a user's finger. In embodiments such as that shown in which the products 14 are in the form of strips, the opening 24 can be located so as to expose a longitudinal end of the top product 14 in the stack, to permit sliding of that product 14 in a longitudinal direction S with respect to the orientation of the products 14 in the stack, and out of the opening 24, during a dispensing operation.

Optionally, the outer surface of the plunger side wall 40 has a perimeter that is substantially similar (i.e., only slightly smaller) in size and shape to the perimeter of the outer surface 32 of the housing outer wall 32. When the plunger 28 advances upwards towards the housing 26, the total height H' of the body 20 is reduced.

The dispenser 10 may include a cap 52 removably affixed to the body 20 over the dispensing portion 22. The cap 52 may serve to retain products 14 within the interior 12 when not being dispensed and/or to protect products 14, such as by providing a sealed environment for storage thereof. In the illustrated embodiment, the cap 52 is pivotally affixed to the body 20 by a hinge 54. The hinge 54 can be of the "living hinge" type, in which the cap 52 and body 20 are formed integrally and connected at a region of sufficiently thin material so as to permit folding therebetween, or the hinge 54 could be a separate mechanical element that joins the cap 52 and body 20.

The cap 52 can optionally be provided with a sealing element to create a moisture and/or airtight seal between the cap 52 and body 20. In the illustrated embodiment, the cap 52 includes a downwardly extending lip seal member 56 that engages an inner surface of the housing outer wall 32. The lip seal member 56 could also or alternatively be configured to engage an outer surface of the inner wall 30. The cap 52 and/or base 20 could also or alternatively be provided with a separate sealing element, such as a gasket.

The cap 52 can also be provided with a thumb tab 58 to facilitate removal from the base 20 when moving the dispenser 10 from a closed position to an opened position. In embodiments such as that shown in the drawings where the cap 52 is connected to the base by a hinge 54, the thumb tab 58 can be provided on the cap at a location opposite that of the hinge 54.

Preferably, there is a moisture tight seal provided between the plunger 28 and the housing 26. For example, sealing elements 60, 62, e.g., made from an elastomer, may be respectively positioned around the perimeters of the outer surface of the housing inner wall 30 and the inner surface of the housing outer wall 32. The sealing elements 60, 62 compress against the side wall 40 of the plunger 28, thereby creating a moisture tight seal between the upper product housing 26 and a lower plunger 28. This seal is maintained while the plunger 28 is stationary and as the plunger 28 is moved upward towards the housing 26.

Optionally, one or more portions of the dispenser could be formed of a desiccant plastic material, such as that disclosed U.S. Pat. Nos. 5,911,937; 6,214,255; 6,130,263; 6,080,350; 6,174,952; 6,124,006; or 6,221,446, all to Hekal, and each of which is incorporated herein by reference as if fully set forth. In one embodiment, the product support 42 is formed of such a desiccant material, but other portions of the dispenser could be formed of a desiccant material as well. Optionally, the dispenser comprises a desiccant material, which may or may not be a desiccant plastic.

The moisture tight seals provided by the sealing elements of the dispenser 10, e.g., between the cap 52 and housing 26 and between the housing 26 and plunger 28, provide a very low moisture ingress rate into the dispenser 10. For example, the dispenser 10 may have a moisture ingress rate of less than 1000 micrograms per day, at 80% relative humidity and 22.2° C. Optionally, at 80% relative humidity and 22.2° C., the moisture ingress rate of the dispenser 10 is 100-1000 micrograms per day, optionally 200-700 micrograms per day, optionally 380-700 micrograms per day, optionally 400-700 micrograms per day, optionally 250-400 micrograms per day, optionally less than 300 micrograms per day.

While the preferred embodiments of the invention have been described in detail above, the invention is not limited to the specific embodiments described, which should be considered as merely exemplary.

What is claimed is:

1. A dispenser for dispensing a plurality of products, the dispenser comprising:

a body, the body including a product housing defining an interior for housing the plurality of products, the product housing being tubular and comprising an outer wall and an inner wall located within the outer wall, the outer wall and the inner wall being joined by a connecting wall, the product housing having a dispensing portion defining a dispensing opening configured to permit the removal of at least one of the plurality of products from the interior, wherein the interior is configured for housing a stack of the plurality of products that extend within the interior towards the dispensing portion;

the body further including a plunger movably engaged with the product housing and including a product support that moves within the interior to move the plurality of products towards the dispensing opening, wherein a portion of the plunger is movably located within a space formed between the inner wall and the outer wall, wherein the plunger comprises a bottom wall located at a lowermost portion of the body and a side wall that extends upwardly from the bottom wall, the sidewall being a portion of the plunger movably located within the space formed between the inner wall and the outer wall;

the dispenser comprising a seal between the plunger and the product housing, wherein elastomeric sealing elements respectively positioned around the perimeters of an outer surface of the product housing inner wall and an inner surface of the product housing outer wall, compress against the side wall of the plunger to create the seal;

the dispenser having a moisture ingress rate of less than 1000 micrograms per day at 80% relative humidity and 22.2° C.

2. The dispenser of claim 1, wherein the plunger is configured to be displaced toward a first end of the product housing to move the plurality of products towards the dispensing portion;

the dispenser further including a ratchet positioned between the side wall and the product housing, the ratchet configured to permit the displacement of the plunger toward the first end of the product housing and prevent displacement of the plunger toward a second end of the product housing;

wherein the dispensing portion is located at an upper area of the product housing and wherein the dispensing portion comprises a top wall that partially closes off the interior.

3. The dispenser of claim 2, wherein the dispensing opening includes angled edges that extend between a top wall of the inner wall of the product housing; and wherein the dispenser opening is configured to both expose a longitudinal end of a product of the plurality of products and permit the sliding of the exposed product from the dispenser opening during a dispensing operation.

4. The dispenser of claim 1, further comprising a cap pivotally affixed to the product housing by a hinge and over the dispensing portion, wherein the cap engages the product housing in a sealed relationship.

5. The dispenser of claim 4, wherein the plunger is configured to be displaced toward a first end of the product housing to move the plurality of products towards the dispensing portion, the body having a total height that is reduced when the plunger is displaced toward the first end of the product housing.

6. The dispenser of claim 1 comprising and/or containing a desiccant material.

7. The dispenser of claim 1, having a moisture ingress rate of 100-1000 micrograms per day at 80% relative humidity and 22.2° C.

8. The dispenser of claim 1, wherein the products are diagnostic test strips, the interior comprising a stack of diagnostic test strips.

9. A dispensing assembly for dispensing a plurality of products provided in a stack, the dispensing assembly comprising:

a body having a plunger, a product housing, a first end, a second end, and an interior, the interior configured for housing the stack, the first and second ends being positioned on opposite ends of the body, wherein the product housing is tubular and comprises an outer wall and an inner wall located within the outer wall, a sidewall of the plunger being movably located within a space formed between the inner wall and the outer wall;

a dispensing portion located at the first end of the body and including a dispensing opening, the plunger configured to move the plurality of products toward the dispensing portion;

a cap pivotally affixed to the body and over the dispensing portion, wherein the cap engages the housing in a sealed relationship;

a seal between the plunger and the product housing, wherein elastomeric sealing elements respectively positioned around the perimeters of an outer surface of the product housing inner wall and an inner surface of the product housing outer wall, compress against the side wall of the plunger to create the seal, the dispensing assembly having a moisture ingress rate of less than 1000 micrograms per day at 80% relative humidity and 22.2° C.; and a ratchet positioned between the plunger and the product housing, the ratchet configured to permit the displacement of the plunger toward the first end of the body to move the stack toward the dispensing opening, the ratchet also configured to prevent the displacement of the plunger toward the second end of the body;

wherein the interior is configured for the stack to extend within the interior toward the dispensing portion, the interior further configured for a selected one of the plurality of products located at an end of the stack to be aligned with the opening, so as to permit removal of the selected one of the plurality of products from the body during a dispensing operation, the dispensing assembly having a total height which is reduced when the plunger moves toward the dispensing portion.

10. The dispensing assembly of claim 9, wherein the products are strips.

11. The dispensing assembly of claim 10, wherein the products are diagnostic test strips, the interior comprising a stack of diagnostic test strips.

12. The dispensing assembly of claim 9, having a moisture ingress rate of 100-1000 micrograms per day at 80% relative humidity and 22.2° C.

13. The dispensing assembly of claim 9, comprising and/or containing a desiccant material.

* * * * *